(12) United States Patent
Saracen et al.

(10) Patent No.: US 7,166,852 B2
(45) Date of Patent: Jan. 23, 2007

(54) TREATMENT TARGET POSITIONING SYSTEM

(75) Inventors: Michael Saracen, Oakland, CA (US); Jay West, Mountain View, CA (US)

(73) Assignee: Accuray, Inc., Sunnyvale, CA (US)

( * ) Notice: Subject to any disclaimer, the term of this patent is extended or adjusted under 35 U.S.C. 154(b) by 43 days.

(21) Appl. No.: 10/881,595

(22) Filed: Jun. 30, 2004

(65) Prior Publication Data
US 2005/0218341 A1 Oct. 6, 2005

Related U.S. Application Data

(60) Provisional application No. 60/560,319, filed on Apr. 6, 2004.

(51) Int. Cl.
*G01J 1/00* (2006.01)
(52) U.S. Cl. .............................. 250/491.1; 250/492.3; 600/424
(58) Field of Classification Search .............. 250/491.1
See application file for complete search history.

(56) References Cited

U.S. PATENT DOCUMENTS

| 5,971,997 A * | 10/1999 | Guthrie et al. .............. 606/130 |
| 2002/0032453 A1 * | 3/2002 | Cosman ...................... 606/130 |
| 2005/0085718 A1 * | 4/2005 | Shahidi ....................... 600/424 |

OTHER PUBLICATIONS

PCT Search Report, International Application No. PCT/US05/11528, International Filing Date Apr. 6, 2005.

PCT Written Opinion of the International Searching Authority, International Application No. PCT/US05/11528, International Filing Date Apr. 6, 2005.

\* cited by examiner

*Primary Examiner*—Nikita Wells
*Assistant Examiner*—Phillip A. Johnston
(74) *Attorney, Agent, or Firm*—Blakely, Sokoloff, Taylor & Zafman LLP

(57) ABSTRACT

A wireless treatment target positioning system for therapeutic radiation treatment includes a patient positioning system and a treatment target locating system. The treatment target locating system includes a room beam coordinate system and a localizing system. The room beam coordinate system includes devices for generating laser beams intersecting at a single point that is spatially coincident with an iso-center of the treatment system. The localizing system includes a movable reference object and a localizer for detecting and determining the position of the movable reference object. A method of positioning a treatment target to the iso-center of the treatment system includes a simulation process and real treatment positioning process. The simulation process includes positioning the treatment target to an iso-center of a simulation system and marking intersection points where laser beams intersect with an exterior of the patient's body. The real treatment positioning process includes determining the position of the intersection points marked on the exterior of the patient body, determining a treatment position for positioning the patient such that the treatment target is aligned with the iso-center of the real treatment system, and positioning the patient to the treatment position.

54 Claims, 8 Drawing Sheets

IR LOCALIZER

PATIENT ISOCENTER LOCALIZATION

CALCULATING TARGET ISOCENTER

POSITION TREATMENT COUCH TO ALIGN
TARGET ISOCENTER TO LINAC ISOCENTER

TREATMENT TARGET POSITIONING SYSTEM

CROSS REFERENCES TO RELATED APPLICATION

This application claims the benefit of priority under 35 U.S.C. §119(e) from co-pending, commonly owned U.S. provisional Patent Application Ser. No. 60/560,319, filed on Apr. 6, 2004, the disclosure of which is incorporated herein by reference.

FIELD OF THE INVENTION

The present invention relates to a therapeutic radiation treatment target positioning system for therapeutic radiation treatment, more particularly, to a system for defining and positioning a treatment target with respect to the iso-center of a therapeutic treatment system.

BACKGROUND

The term radiosurgery refers to a procedure in which intense and precisely aimed doses of radiation are delivered to a target region in a patient, in order to destroy tumor cells or otherwise treat the target region. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in radiosurgical sessions. For convenience, the term "radiosurgery" in this application shall henceforth mean "radiosurgery and/or radiotherapy." Both radiotherapy and radiosurgery are referred to herein as "therapeutic radiation treatments."

In radiosurgery, it is necessary to control the position of the radiation source so that its beam or beams can be precisely directed to the target tissue while minimizing irradiation of surrounding healthy tissue. It is also necessary to determine with precision the position of the target region (and surrounding critical structures) relative to the reference frame of the treatment device.

The patient is usually placed on a support device, such as a couch or a table. During treatment, if an imaging system is provided, it repeatedly measures the position and orientation of the target relative to the x-ray source. The patient is then positioned by the support device controlled automatically or manually by an operator, so that the treatment target inside the patient body is aligned with respect to an iso-center of the radiation source to ensure that therapeutic radiation is applied to the treatment target within the patient.

It is required that the iso-center of the target treatment area be defined and positioned accurately in order to provide the desired treatment. One method currently used to identify the tumor position for treatment is through the use of a diagnostic x-ray or fluoroscopy system to define and align the iso-center of the treatment area to the iso-center of the radiation source.

While operating these image-guided systems, it is necessary to adjust the position and orientation of the patient in order to ensure that the target within the patient remains properly aligned with respect to the treatment beam. The position and orientation of the patient must be periodically adjusted, for example, in order to compensate for any motion (such as respiratory motion, sneezing, or shifting) that the patient may undergo during treatment. In the currently used image-guided systems, the image of the patient or the treatment area and the ambient area has to be taken many times during the operation to detect any misalignment of the iso-center of the treatment area from the iso-center of the therapeutic treatment system caused by patient movement, and to adjust the alignment.

Therefore, it is desirable to provide a new system for defining and positioning a treatment target with respect to the iso-center of the therapeutic treatment system that minimizes and optimizes the processes required for accurately positioning the patient during the operation.

SUMMARY OF THE INVENTION

The present invention provides a wireless or wired treatment target positioning system adapted for use with therapeutic radiation treatment systems. A therapeutic radiation treatment system generally includes a gantry-based or robotic-based linear accelerator (LINAC) system. The wireless or wired treatment target positioning system includes a patient positioning system and a treatment target locating system.

Any patient positioning system can be used with the wireless or wired treatment target positioning system. In one preferred embodiment, the patient positioning system is a robotic positioning assembly, for example, a robotic couch assembly, which includes a robotic positioning device (a robot couch) for supporting and moving the patient and a controller for controlling the movement of the robot couch. The controller is loaded with information about the location of an iso-center of the LINAC system in a treatment coordinate system.

The treatment target locating system preferably includes a room beam coordinate system and a localizing system. The room beam coordinate system is used to facilitate calibration of the iso-center of the treatment area (treatment target) with the iso-center of LINAC system. Preferably, the room beam coordinate system includes devices for generating laser beams, for example three laser beams, intersecting at a single point that is either coincident with, or whose position is known with respect to, the iso-center of the LINAC system. The localizing system can be an infrared localizing system, or other localizing system, for example, a localizing device using ultrasonic technology. In one preferred form, the localizing system includes a movable reference object and a localizer for detecting and determining the position of the movable reference object.

In a preferred embodiment according to the present invention, the treatment target locating system is an infrared localizing system. In this embodiment, the movable reference object includes an infrared emitting device, and the localizer includes infrared cameras.

In one preferred embodiment, the movable reference object is an infrared emitting probe extending along a longitudinal axis. The infrared emitting probe has a distal tip which has a pre-defined location based on the probe geometry. A series of light emitting diodes (LED's) are embedded in the probe in a pre-defined geometric orientation. The infrared (IR) localizer includes one or more infrared cameras, preferably two or three infrared cameras, which work in conjunction with each other to identify a point of infrared light emitted from the emitting probe, and determine its location with respect to the treatment coordinate system. The series of LED's in the probe flash in a pre-defined sequence, so that the localizer is able to identify the emitting probe and its position and orientation. The infrared emitting probe can be a wireless device or a wired device. The localizer transmits the position and orientation information of the infrared emitting probe to a computer system, which is programmed to determine the location of the distal tip of the emitting probe with respect to the treatment coordinate system based on the information received from the localizer and the location information of the distal tip in the probe geometry.

A complete therapeutic radiation operation involves obtaining a preoperative CT scan data of the patient to show the position of the tumor that will be treated. Alternatively, MRI (magnetic resonance imaging), X-ray, or fluoroscopy may be used to obtain the preoperative imaging data. The preoperative imaging data can be imaging data obtained before the operation or an imaging data obtained in a previous treatment. Based on the preoperative imaging data, an approximate treatment location for the patient is computed and a treatment plan is generated. The imaging data and the treatment plan are loaded into the controller of the robot couch assembly, so that the robot couch assembly knows the approximate treatment position with respect to the treatment coordinate system.

Before the real treatment, a simulation process is performed using a simulation system. The iso-center of the simulation system is calibrated to the iso-center of the real treatment system (the LINAC). The location information of the iso-center of both the simulation system and the real treatment system is loaded into the controller of the robot couch assembly.

The laser beams are directed to the single point which is coincident with the iso-center of the simulation system or whose position with respect to the iso-center is determinable. The robot couch assembly, with the controller knowing the location of the iso-center of the simulation system and the approximate location of the treatment area, positions the target treatment area approximately with respect to the iso-center of the simulation system. Then a near real time image system, e.g. an x-ray imaging system, which is connected to the controller of the robot couch assembly, is used to generate near real time imaging data to facilitate precise positioning of the treatment target with respect to the iso-center of the simulation system. The treatment target preferably is the iso-center of the treatment area.

Once the target is aligned with the single point where the laser beams converge (preferably the iso-center of the simulation system), skin tattoos or other indelible markings are marked on the patient at the points where the laser beams intersect on the exterior skin of the patient. The tattoos or indelible markings may also be made at points where the laser beams intersect with an immobilization device, which is used to support the patient. The immobilization device preferably is a body mold to fit the patient's body curve, or a mask for head treatment. The body mold or mask is preferably made from a moldable material. The body mold or mask is customized for each particular patient and is attached on the top of the robot couch for support of the patient. The three laser beams preferably are arranged such that one beam intersects with the skin of the patient on the left side of the patient, one intersects with the skin on the right side of the patient, and one on the anterior or posterior aspect of the patient, depending on the patient being treated in a prone or a supine orientation. The treatment target that is aligned with the iso-center of the simulation system is the intersection point of the three laser beams.

Alternatively, tracking systems other than laser beams may be used to facilitate locating the treatment target. Exemplary tracking systems include, but not limited to, magnetic tracking system, ultrasound tracking system, and the like.

In real treatment operation, according to one preferred embodiment of the present invention, the operator uses the distal tip of the infrared emitting probe to touch the markings, which have been placed on the patient body in the previous simulation process, in a pre-defined order (e.g., left, right, top). As each point is touched, the infrared camera system records the tip position of the infrared emitting probe, and the computer system computes the position of the touched point in the treatment coordinate system. Once the three points have been touched and the position information of these three points is transferred to the computer system, the computer system uses a triangulation software to determine the position and orientation of the treatment target based on the position information of these three points. Alternatively the user may select one or two points to determine only translational (x-, y-, and z-) orientation without correcting for rotations.

The iso-center locating system is integrated with the patient positioning system in order to complete the desired outcome of automated patient alignment. The position information of the iso-center of the target treatment area obtained through the iso-center locating system is transmitted to the computer controller of the robot couch assembly. The robot couch assembly, which has been preprogrammed with the position information of the iso-center of the LINAC system and the trajectories of the laser beams, then positions the iso-center of the treatment area with respect to the iso-center of the LINAC system. The operator can confirm the patient position by matching the markings on the patient body to the points where the laser beams intersect with the skin of the patient body. The operator also can make any fine tune adjustments with a hand panel controller of the robot couch assembly. After the fine tune adjustment, the therapeutic treatment system is then ready for treating the patient.

DETAILED DESCRIPTION

Figure 1:
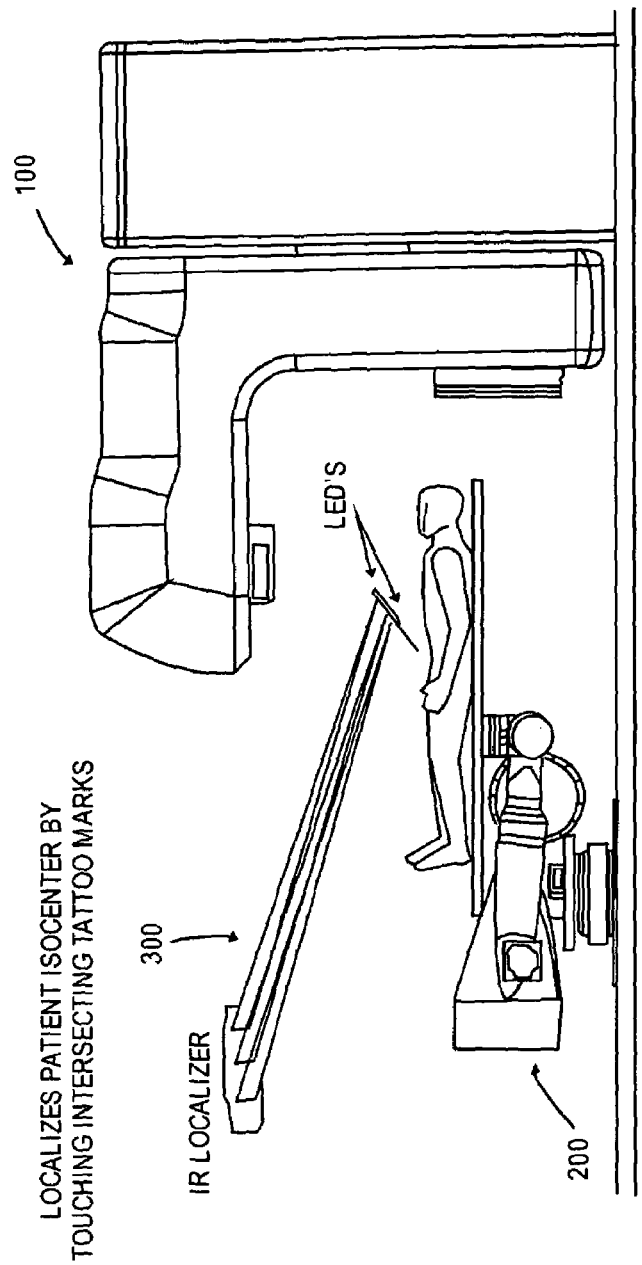
FIG. 1 schematically illustrates a treatment target positioning system used with a therapeutic radiation treatment machine according to one preferred embodiment of the present invention.

A therapeutic radiation treatment system that can be used with the wireless or wired treatment target positioning system in accordance with the present invention is illustrated in FIG. 1. The therapeutic radiation treatment system includes a gantry-based LINAC system 100. In the exemplary embodiments described in the disclosure and shown in the drawings, the treatment target positioning system is used with a gantry-based LINAC system, but a person skilled in the art should understand the treatment target positioning system can also be used with a robotic-based LINAC system. The wireless or wired treatment target positioning system includes a patient positioning system 200 and a treatment target locating system 300. The treatment target is generally defined in a simulation process or in a previous treatment process. Preferably, the treatment target is defined at the iso-center of the treatment area, but the position of the treatment target can vary in one treatment process or in different treatment processes for a patient.

The patient positioning system 200 is preferably a robotic positioning assembly, for example, a robot couch assembly, which includes a robotic positioning device (a robot couch) for supporting and moving the patient and a controller for controlling the movement of the robot couch. The controller is loaded with information of the location of the iso-center of the gantry-based LINAC system 100 in a treatment coordinate system.

The treatment target locating system 300 preferably includes a room beam coordinate system and a localizing system. The room beam coordinate system is used to facilitate calibration of the iso-center of the treatment area (treatment target) with the iso-center of the LINAC system. Preferably, the room beam coordinate system includes devices for generating laser beams, for example three laser beams, intersecting at a single point. The location of the point with respect to the iso-center of the LINAC system is known. Preferably, the single point is spatially coincident with the iso-center of the LINAC system. The localizing system can be an infrared localizing system, or other localizing system, for example, a localizing device using ultrasonic technology, or using magnetic or gyroscopic tracking devices. In one preferred form, the localizing system includes a movable reference object and a localizer for detecting and determining the position of the movable reference object. The treatment target locating system 300 is adapted to detect the position of the iso-center of the treatment area. Details of the treatment target locating system 300 will be described later in this disclosure.

The treatment target locating system 300 is operatively connected to the controller of the patient positioning system 200 to transmit the location information of a treatment target inside the patient to the controller. In one preferred embodiment, the treatment target locating system 300 uses a wireless (or wired) infrared tracking system to locate the position of the treatment target in the treatment area and relays this information to the controller of the robot couch assembly. The robot couch assembly then positions the treatment target to the iso-center of the LINAC system for radiation treatment of the treatment area.

The treatment involves obtaining a preoperative CT scan data of the patient to show the position of the tumor that will be treated. Alternatively, MRI (magnetic resonance imaging) PET, X-ray, ultrasound or fluoroscopy may be used to obtain the preoperative imaging data. The preoperative imaging data can be imaging data obtained in a previous treatment. Based on the preoperative imaging data, an approximate treatment location for the patient is computed and a treatment plan is generated. The imaging data and the treatment plan are loaded into the controller of the robot couch assembly 200, so that the robot couch assembly knows the approximate treatment location with respect to the treatment coordinate system.

Before the real treatment, a simulation process is performed using a simulation system. The iso-center of the simulation system is calibrated to the iso-center of the real treatment system (the LINAC). A room beam coordinate system is used to facilitate calibration of the iso-center of the treatment area (the treatment target) with the iso-center of the simulation system in the simulation process. Preferably, the room beam coordinate system includes devices for generating laser beams, for example three laser beams 302 shown in FIG. 2, intersecting at a single point that is spatially coincident with the iso-center of the simulation system. The location information of the iso-center of the simulation system is loaded into the controller of the robot couch assembly 200. The robot couch assembly 200, with the controller knowing the location of the iso-center of the simulation system and the approximate location of the treatment area, positions the target treatment area approximately to the iso-center of the simulation system. Then a near real time image system, e.g. an x-ray imaging system, which is connected to the controller of the robot couch assembly 200, is used to generate near real time imaging data to facilitate precisely positioning of the treatment target to near the iso-center of the simulation system.

Figure 2:
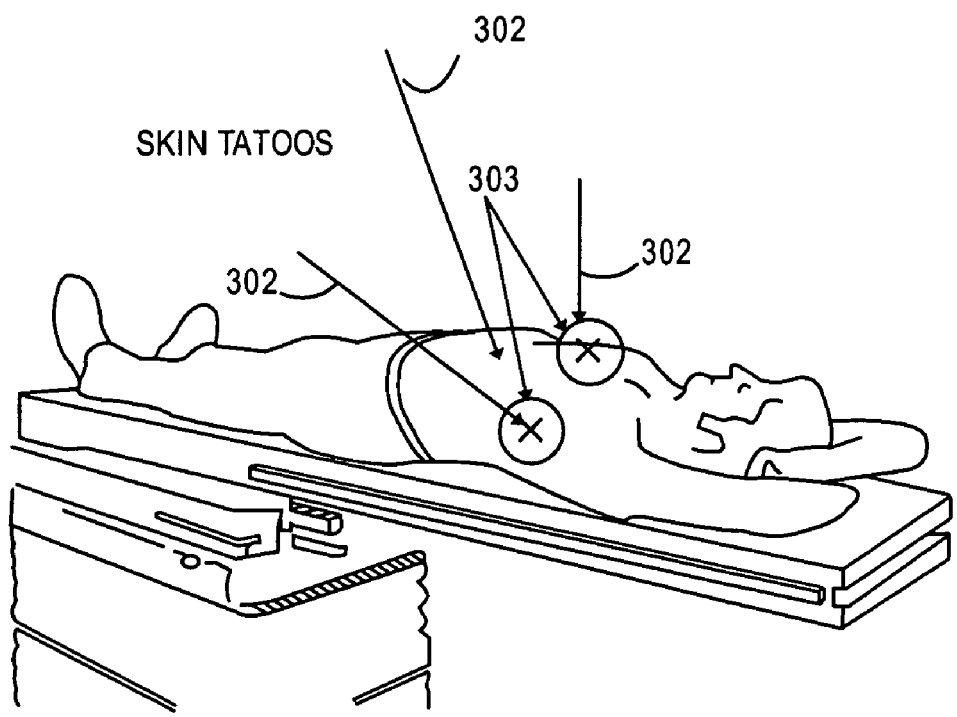
FIG. 2 is a schematic view of a patient with skin markings on the exterior of the patient body.

Once the target is aligned to the iso-center of the simulation system, reference objects 303, for example, skin tattoos or other indelible markings, are placed on the patient at the points where the laser beams 302 intersect on the exterior skin of the patient, as shown in FIG. 2. In an alternative and equivalent form, the tattoos or indelible markings may also be made at points where the laser beams 302 intersect with an immobilization device, which is used to support the patient. The immobilization device preferably is a body mold to fit the patient's body curve or a mask for head treatment. The body mold or mark is preferably made from a moldable material. The body mold or mask is customized for each particular patient and is attached on the top of the robot couch to support the patient. The immobilization device is generated in a simulation or pre-treatment process, and can be used in subsequent treatment processes.

The size or shape of the treatment area or the patient body may change over the course of subsequent treatment, and that change may cause displacement of the treatment target from the defined location. In one preferred embodiment, the system is able to perform a verification step to check whether the location of the treatment target has changed. If the displacement of the treatment target is greater than a tolerance value, the system notifies the user or operator that another simulation process is needed to change the location of the markings.

The three laser beams 302 preferably are arranged such that one beam intersects with the skin of the patient on the left side of the patient, one intersects with the skin on the right side of the patient, and one on the anterior or posterior aspect of the patient, depending on the patient being treated in a prone or a supine orientation. The treatment target that is aligned with the iso-center of the simulation system (or the iso-center of the LINAC in real treatment operation) is coincident with the intersection point of the three laser beams. The exemplary embodiments illustrated in the figures and the description use three laser beams to facilitate positioning the patient. A person skilled in the art should appreciate that less or more laser beams can be used. In an alternate form, the LINAC system can generate laser beams to facilitate precise positioning of the treatment target.

Alternatively, tracking systems other than laser beams may be used to facilitate locating the treatment target. For example, a magnetic tracking system may be used. The magnetic tracking system may include a magnetic sensing system, and the reference objects on patient body or on the immobilization device may include at least one magnetic signal generator attached to the patient body or the immobilization device. When the treatment target is aligned with a point, whose position with respect to the iso-center is determinable, the magnetic tracking system records the position of the magnetic signal generator. In real treatment, the patient positioning device uses the data recorded by the magnetic tracking system to position the patient to the treatment position.

The real treatment system is substantially identical to the simulation system except that the therapeutic radiation beam energy of the real treatment system is much higher than the beam energy of the simulation system. It may take 30 to 60 minutes to optimize the real treatment system for a particular patient. By using a simulation process, the optimization process can be performed on the simulation system, and thus the optimization time on the real treatment system can be substantially reduced. A person skilled in the art should understand that using the simulation system to optimize patient alignment is a preferred approach, but not necessary. The simulation process as described above also can be performed on the real treatment system.

Figure 3:
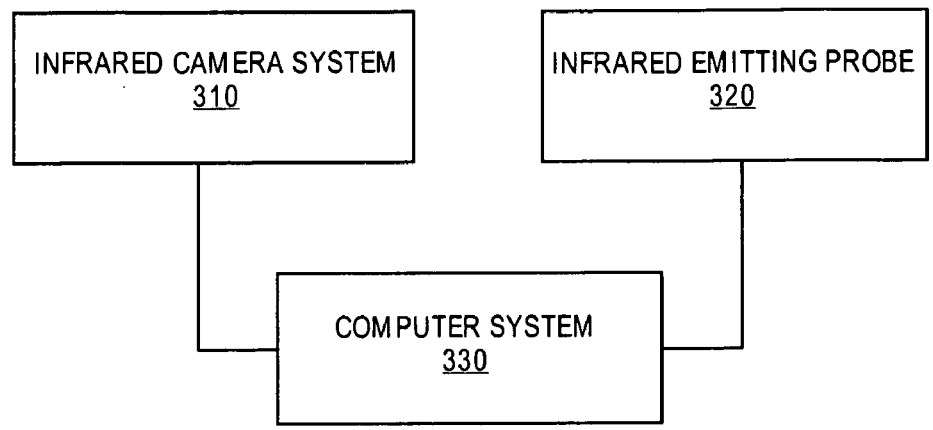
FIG. 3 is a schematic diagram of a localizing system of the target positioning system according to one aspect of the present invention.
Figure 4:
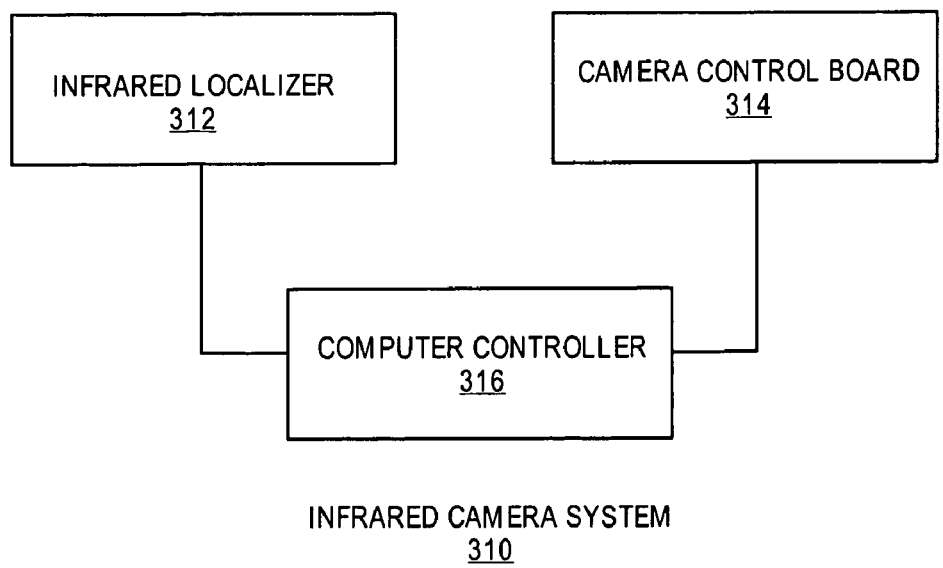
FIG. 4 is a schematic diagram of an infrared camera system of the localizing system according to one aspect of the present invention.

In a preferred embodiment according to the present invention, the treatment target locating system 300 is an infrared localizing system. In this embodiment, the movable reference object includes an infrared emitting device, and the localizer includes infrared cameras. FIG. 3 illustrates a diagram of one exemplary embodiment of the treatment target locating system 300, which is an infrared localizing system according to one aspect of the present invention. As shown in FIG. 3, the treatment target locating system 300 includes an infrared camera system 310 and a movable reference object, for example, an infrared emitting probe 320. As shown in the diagram in FIG. 4, the infrared camera system 310 includes an infrared localizer 312, a camera control board 314, and a computer controller 316. An operator can control the infrared camera system 310 through the camera control board 314 and/or the computer controller 316. The infrared emitting probe 320 has a distal tip 322 which has a pre-defined location based on the probe geometry. A series of light emitting diodes (LED's) are embedded in the probe in a pre-defined geometric orientation. The infrared (IR) localizer 312 includes one or more infrared cameras, preferably two or three infrared cameras, which work in conjunction with each other to identify a point of infrared light emitted from the emitting probe 320, and determine its location with respect to the treatment coordinate system. The series of LED's in the probe flash in a pre-defined sequence, for example, starting from the LED nearest to the proximal end of the emitting probe 320 to the LED near or at the distal tip 322 of the emitting probe 320, so that the localizer 312 is able to identify the emitting probe 320 and its position and orientation. The infrared emitting probe 320 can be a wireless device or a wired device. The localizer 312 transmits the position and orientation information to the computer controller 316 of the infrared camera system 310, which thus determines the location of the distal tip 322 of the emitting probe 320 with respect to the treatment coordinate system based on the information received from the localizer 312 and the location information of the distal tip 322 in the probe geometry.

Figure 5:
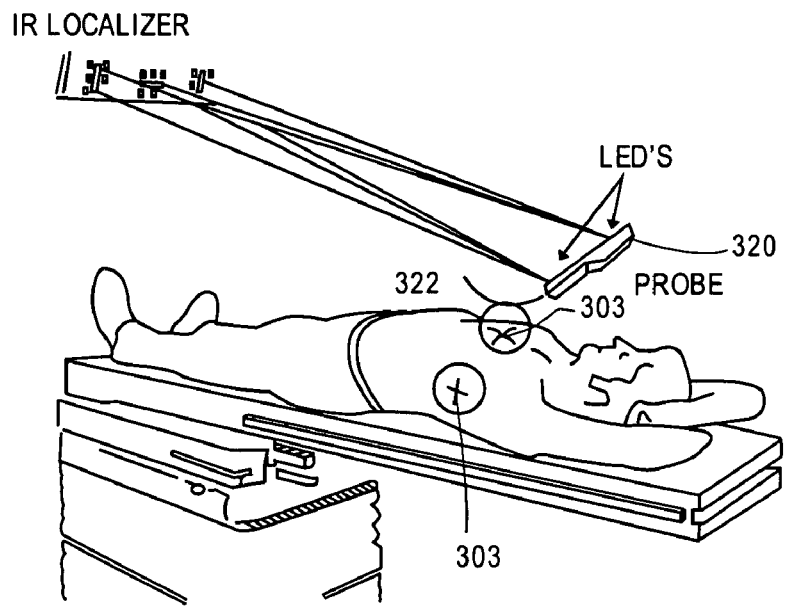
FIG. 5 is a schematic view of a treatment target positioning system according to one preferred embodiment of the present invention.
Figure 6:
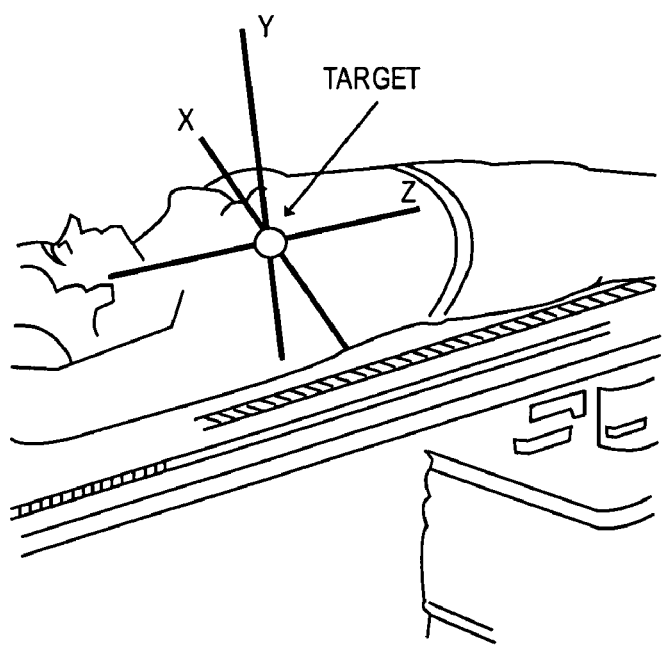
FIG. 6 schematically illustrates a patient with a treatment target defined in the patient anatomy.

In real treatment operation, according to one preferred embodiment of the present invention and as shown in FIG. 5, the operator uses the distal tip 322 of the infrared emitting probe 320 to touch the markings 303, which have been placed on the patient body in a previous simulation process, in a pre-defined order (e.g., left, right, top). As each point is touched, the infrared camera system 310 records the position of the infrared emitting probe 320, and the computer controller 316 computes the position of the touched point in the treatment coordinate system. Alternatively the user may select one or two points to determine only translational (x-, y-, and z-) orientation without correcting for rotations. Once the points have been touched and the position information of these points is transferred to a computer system 330, which is pre-loaded with the information of the trajectories of the laser beams and uses a triangulation software to determine the position of the treatment target based on the position information of these points. The treatment target preferably is the iso-center of the treatment area as defined in the previous simulation process or in a pre-treatment process. The computer system 330 and the computer controller 316 can be integrated into one system, or are separate systems.

Figure 7:
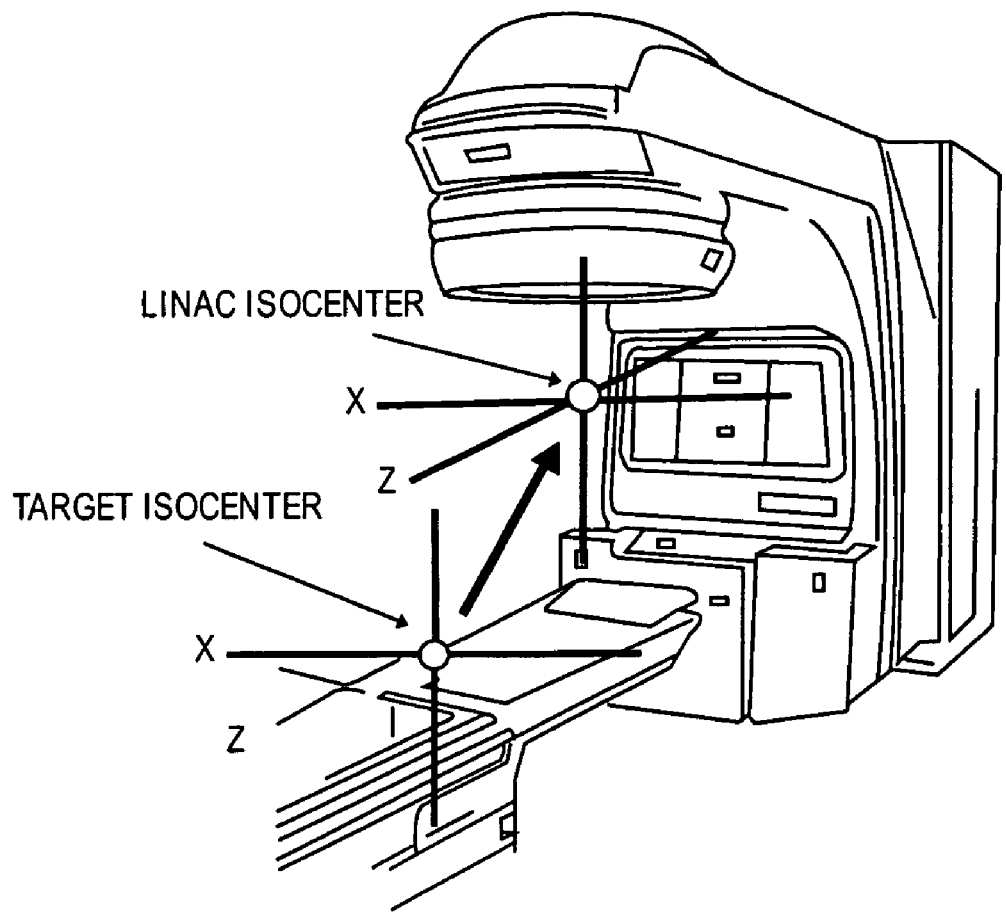
FIG. 7 schematically illustrates the treatment target and the iso-center of the treatment system in a treatment coordinate system.

The iso-center locating system 300 is integrated with the patient positioning system 200 in order to complete the desired outcome of automated patient alignment. The position information of the iso-center of the target treatment area obtained through the iso-center locating system 300 is transmitted to the computer controller of the robot couch assembly 200. As shown in FIG. 7, the robot couch assembly 200, which has been preprogrammed with the position information of the iso-center of the LINAC system and the trajectories of the laser beams, then positions the iso-center of the treatment area with respect to the iso-center of the LINAC system. The operator can confirm the patient position by matching the markings on the patient body to the points where laser beams intersect with the skin of the patient body. The operator also can make any fine tune adjustments with a hand panel controller of the robot couch assembly 200. After the fine tune adjustment, the therapeutic treatment system is then ready for treating the patient.

Figure 8:
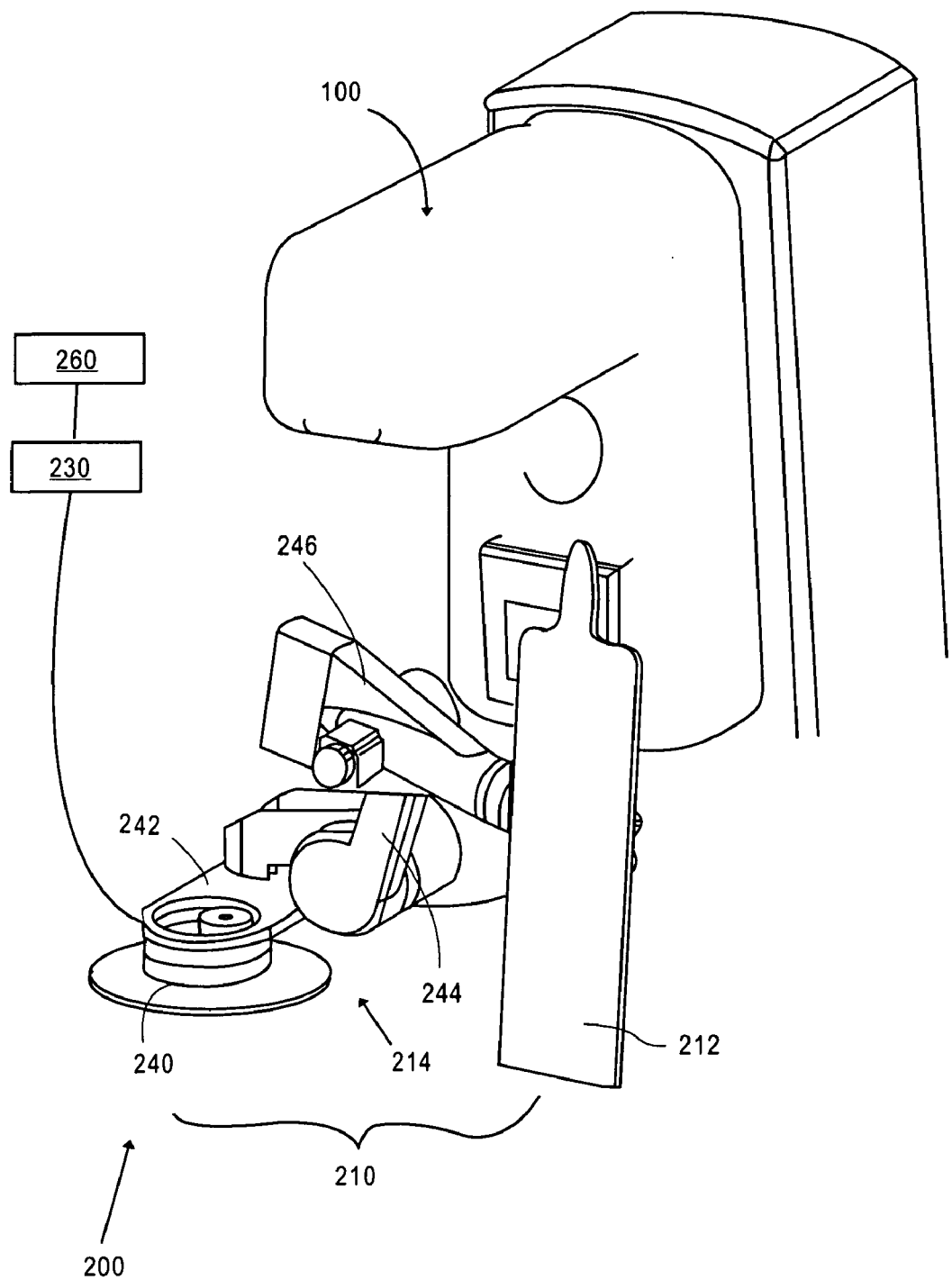
FIG. 8 schematically illustrates a robotic positioning device with a therapeutic treatment system.

FIG. 8 illustrates an exemplary robot couch assembly 200 used with the wireless or wired treatment target positioning system in accordance with one preferred embodiment of the present invention. In overview, the robot couch assembly 200 includes: 1) a support device (robot couch) 210, which includes a supporting means 212 controlled by a robot 214, for supporting the patient during treatment; and 2) a controller 230 including a control computer. The controller 230 is operatively connected to and communicates with the robot couch 210, and is adapted to control the motion of the robot couch 210.

In the illustrated embodiment, the supporting means 212 is a treatment table, although in other embodiments, other types of support devices (such as a chair or bench) may be used. The supporting table 212 is capable of motion in at least three degrees of freedom, namely three translational degrees of freedom (x-, y-, and z-). Preferably, the table 212 is capable of motion in all six degrees of freedom, namely three translational degrees of freedom plus three rotational degrees of freedom (roll-, pitch-, and yaw-rotations). The motion command signal, generated by the controller 230, thus controls corrective motions of the table 212 in at least three, and preferably six, degrees of freedom.

In one preferred embodiment, the support device 210 is adapted to provide loading positions for loading or unloading the patient, preferably in horizontal and/or vertical manners. One vertical loading/unloading manner of the supporting table 212 is shown in FIG. 8. In one preferred form, the supporting surface of the robot-controlled table 212 is provided with an immobilization device, namely a patient specific mold, which is customized to fit the body curve of the patient. In another preferred form, one end of the supporting table is provided with a footplate for supporting the patient's feet in vertical loading manners.

As shown in FIG. 8, the robot 214 includes a base 240, a plate member 242, a first arm 244, and a second arm 246. The base 240 is secured on a plinth or the floor of the treatment room during treatment. The plate member 242 is rotatably mounted on the base 240. A first end of the first arm 244 is rotatably connected to the plate member 242. A first end of the second arm 246 is rotatably connected to a second end of the first arm 244. The treatment table 212 is rotatably attached to a second end of the second arm 246 at approximately a middle portion of the treatment table 212. The arrangement of the base 240, the plate member 242, the first arm 244, and the second arm 246 provides the treatment table 212 with six-degrees of freedom. The relative movement between any two connected members, which are rotatably or rotatably connected, can be controlled by the control computer 230 of the robot couch assembly 200. The robot couch assembly 200 can position the patient on the treatment table in any place in a reachable area and can provide any loading/unloading position for a particular patient in that reachable area.

Figure 9:
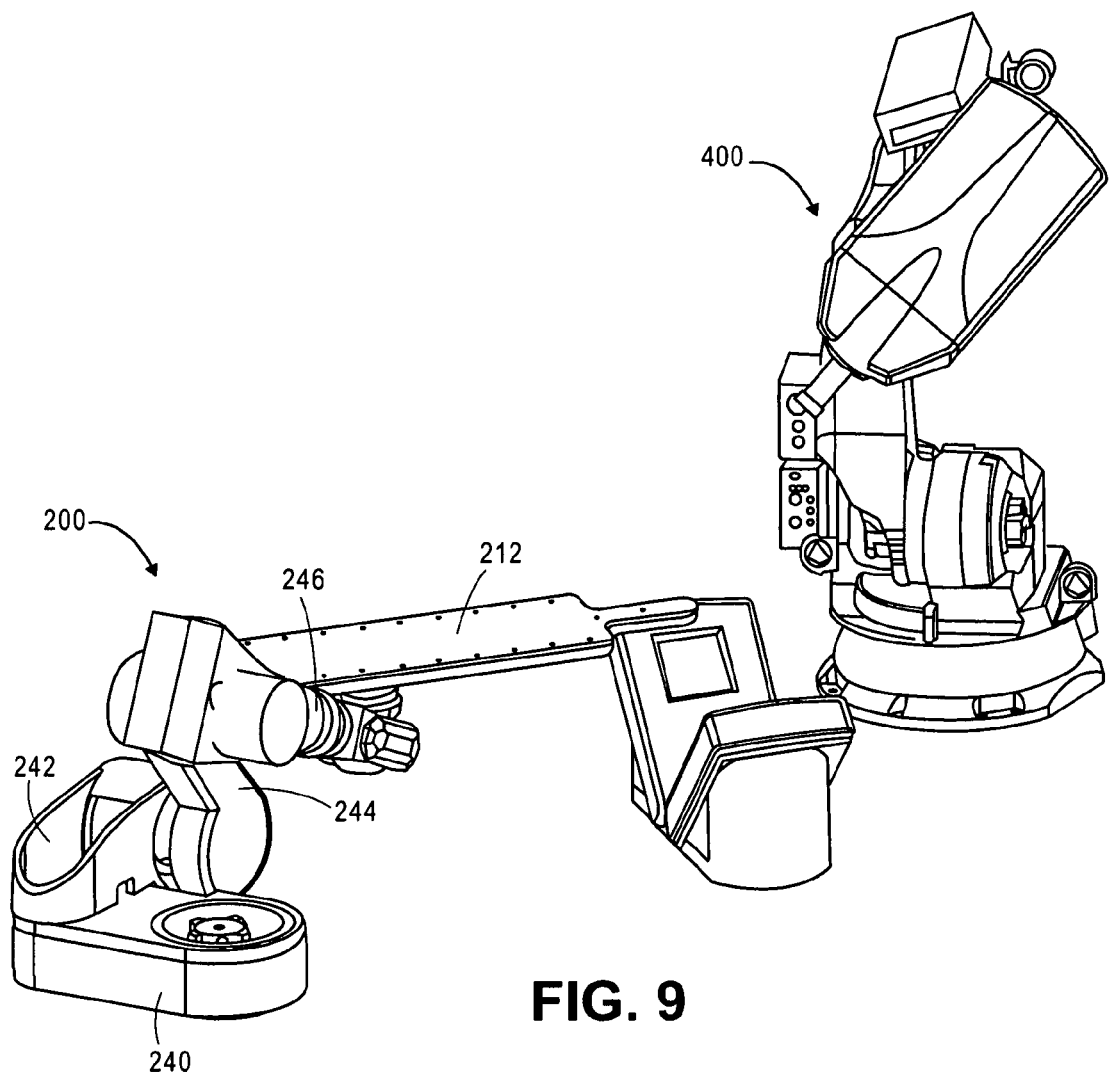
FIG. 9 illustrates a perspective view of a patient positioning assembly together with a CyberKnife® radiosurgery system.
Figure 10:
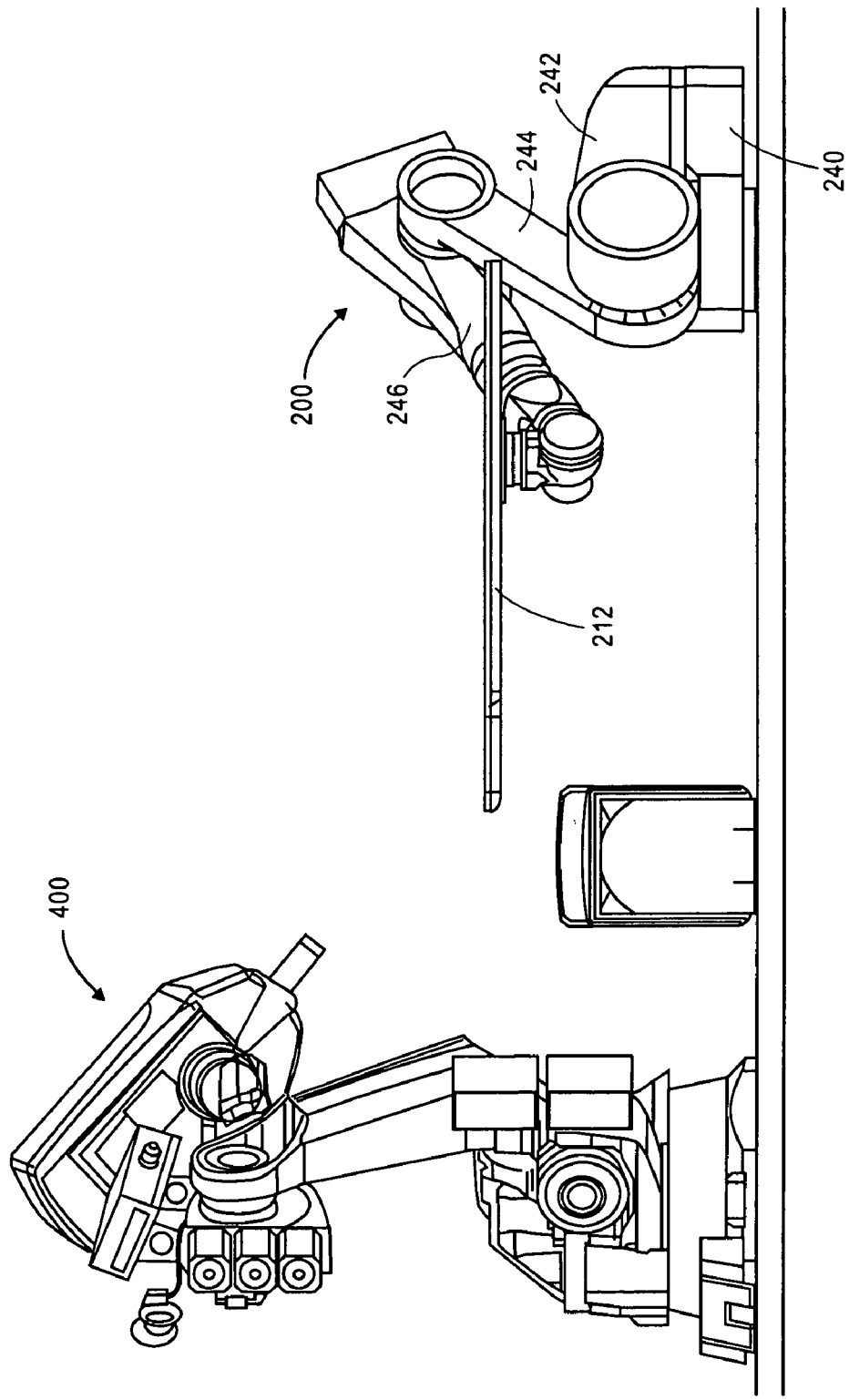
FIG. 10 illustrates a perspective side view of a patient positioning assembly together with a CyberKnife® radiosurgery system.

FIGS. 9 and 10 illustrate another exemplary embodiment of the robot couch assembly 200 together with a CyberKnife® radiosurgery system 400. The robot couch assembly in FIGS. 9 and 10 are substantially the same as the robot couch assembly illustrated in FIG. 8, except that in the robot couch assembly in FIGS. 9 and 10, the base 240 is rotatably mounted on the floor, or alternatively, the base 240 is rotatably mounted to a plinth, which is secured on the floor, or within or under the floor.

A person skilled in the art should appreciate that more rotatable and/or slidable sections, for example, a third arm, can be added to the robot couch assembly to obtain more flexibility and a greater reach of the robot couch. Alternatively, the robot couch assembly can include fewer sections than the robot couch assembly shown in FIG. 8 and FIGS. 9 and 10, for example, including only one arm section instead of two arms. These specific forms should be considered equivalent to the present invention.

The controller 230 includes a comparator, or other software for comparing the position of the iso-center of the target treatment area, as calculated by the control computer of the wireless or wired treatment target positioning system with the iso-center of the LINAC treatment system. The controller 230 computes the amounts of translation (in three degrees of freedom) and rotation (in three degrees of freedom) that are required in order to position the treatment target to substantially match the position of the iso-center of the LINAC treatment system. The controller 230 includes software for converting this information into one or more units of motion of the table 212 (implemented by the motions of the plate member 242, the first arm 244, the second arm 246, and the table 212), in at least three degrees of freedom, and preferably in six degrees of freedom.

In one embodiment, the robot couch assembly 200 further includes at least one user interface 260, including one or more user interface units that enable a user or operator to interactively participate in controlling the motion of the support device.

The user interface 260 effects computer control of the six degrees of freedom of the robot-controlled table 212. In a particular embodiment, the user interface unit is a remote control unit that provides a user with remote control capabilities for remote control of the motion of the support device 210. In an alternative form, the user interface includes one or more user interface screens on the user control console of a workstation, allowing the user to inspect, initiate, and interactively control the table motion to position the patient. The user interface screen provides to the user an integrated table position display, and table motion control capabilities. The user interface screen may provide sub-options to adjust translations only, or rotations only or all the degrees of freedom available together. Further information about the exemplary robot couch assembly 200 is disclosed in U.S. patent application titled: PATIENT POSITIONING ASSEMBLY, invented by Michael Saracen, et al., Ser. No. 10/881,315, which is incorporated herein by reference. The above-described robotic patient positioning system is an exemplary patient positioning device used with the present invention. Other patient positioning devices also can be used, for example, the patient positioning device disclosed in U.S. patent Ser. No. 10/687,860, titled PATIENT POSITIONING ASSEMBLY FOR THERAPEUTIC RADIATION, invented by Eric Earnst, et al., which is also incorporated herein by reference.

A person skilled in the art should understand that the computer controller 316, the computer system 330, the control system 230 of the robotic positioning system 200, and the computer control system of the simulation system and the real treatment LINAC system can be separate computer systems, and alternatively, any two or more, or all of them can be integrated into one computer system. Any possible embodiments and any combinations regarding the computer systems should be considered within the meaning and range of equivalency of the claims in the subject application.

A person skilled in the art also should appreciate that the treatment coordinate system and the room beam coordinate system, and any other coordinate system used in the simulation process, in the real treatment process, and/or any other pre-treatment process, can be one coordinate system, or different coordinate systems, and if they are different systems, the computer systems described above can be programmed to convert from one coordinate system to another coordinate system. Any possible embodiments regarding the coordinate systems should be considered within the meaning and range of equivalency of the claims in the subject application.

Following is a description of the operation of the treatment target position system described above.

Prior to the therapeutic radiation treatment, the position of the treatment target, which preferably is an iso-center of a treatment area, is first identified in a simulation process. The simulation may use CT or MRI scan or by X-ray or fluoroscopy to locate the position of the treatment target. During the simulation process, the iso-center of the target treatment area is aligned to the iso-center of the simulation machine. Markings are placed on the patient's skin and/or the immobilization device at points where the laser beams, which are directed to or in proximity to the iso-center of the simulation machine, intersect with the patient's body and/or the immobilization device.

At the beginning of the real treatment, the patient is brought into the treatment room and placed on the robot couch. The operator uses an infrared localizer and infrared emitting probe to identify the positions of the skin markings.

The treatment target position system then determines the iso-center of the target treatment area as defined in the simulation process and sends the information representative of the location of the iso-center of the treatment area to the control computer of the robot couch assembly, which calculates the transformation (rotation and translation) through which the patient needs to be moved so that the treatment target can be aligned to the iso-center of the real treatment system. Alternatively, instead of matching the treatment target to the iso-center of the LINAC system, the computer system may be programmed to directly calculate the transportation needed for the patient to align each of the skin markings along the line of the corresponding laser beam. In each method, because errors may occur in the measurements of the position of the skin markings, part or all of the markings may not be precisely positioned in the line of the corresponding laser beams. An iterative algorithm, which is called "the Iterative Closest Point Algorithm" and was developed by Besl & McKay, is used to minimize the sum of the squared distances of each point from the line of the corresponding laser beam. The algorithm is published in "A method for Registration of 3D Shapes", IEEE Transactions on Pattern Analysis and Machine Intelligence, Vol. 14, pages 239–256, 1992. The computer system of the robot couch assembly may be programmed with software to implement the algorithm to optimize positioning of the patient.

Since the robot couch assembly 200 knows the position of the treatment target through the treatment target locating system 300, and also knows the position of the iso-center of the LINAC system, the robot couch assembly 200 automatically positions the treatment target to the iso-center of the LINAC in a way that the treatment target within the patient's anatomy remains properly coincident with the iso-center of the LINAC treatment system throughout the treatment procedure.

In one preferred form, the robot couch assembly 200 is adapted to detect the misalignment of the treatment target with the iso-center of the LINAC caused by patient's movement by comparing the position of the treatment target with the iso-center of the LINAC, and automatically adjust the position of the treatment target to align the target with the iso-center of the LINAC.

The wireless/wired treatment target positioning system also can be used with a robotic-based therapeutic radiation treatment system, which includes a robot arm having a therapeutic radiation source mounted at a distal end of the robot arm for selectively emitting therapeutic radiation. The controller 230 of the robot couch assembly 200 preferably is connected to the robot-based radiation therapeutic treatment system and controls the motion of the x-ray source, as well as the motion of the supporting table 212. In other words, the controller 230 controls the relative motion of the supporting table 212, with respect to the robot-implemented motion of the x-ray source. In this way, the patient positioning assembly 200 is capable of dynamically controlling the motion of the support device 210, so as to implement any trade-off motions that are necessary for correctly aligning the patient relative to the treatment beam, and for delivering the correct radiation pattern to the target. In one embodiment, the combination of the motions of the supporting table 212 and the motions of the x-ray LINAC, are dynamically coordinated and controlled, so as to maximize the workspace available to the therapeutic radiation treatment system.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for determining the location of a treatment target in a treatment area within a patient's anatomy to allow alignment of the treatment target with the iso-center of a therapeutic radiation treatment device, said system comprising: means for generating laser beams, which are directed to and intersect at an intersection point, wherein the location of said intersection point with respect to the iso-center of the therapeutic radiation treatment device is determinable;
   a localizing system comprising:
      a). a movable reference object comprising a distal tip;
      b). a localizer comprising at least one detector and a computer system for detecting and determining the position of said moveable reference object in a treatment coordinate system when said moveable reference object is positioned at a series of positions, wherein the position of the distal tip of the movable reference object with respect to a geometry of said reference object is loaded in the computer system of said localizer, wherein said computer system of said localizer is adapted to determine the position of the distal tip in said treatment coordinate system based on the position of said movable reference object and the position of said distal tip with respect to the geometry of said reference object; and
   wherein said movable reference object is adapted to be positioned at a series of predefined points on said patient body to determine the position of said series of points in said treatment coordinate system by said localizer,
   wherein said series of predefined points on said patient body are obtained in a pre-treatment process, said predefined points representative of intersection points of said laser beams with an exterior of the patient's body when said treatment target in said treatment area is positioned coincident with said intersection point of said laser beams, and
   wherein said computer system of said localizer is programmed with a software for determining the position of said treatment target in said treatment coordinate system based on the position information of said series of said predefined points on said patient body received from said localizing system.

2. A system according to claim 1, wherein said localizing system is an infrared localizing system.

3. A system according to claim 1, wherein said at least one detector comprises at least one infrared camera.

4. A system according to claim 1, wherein said laser beams comprises three laser beams, and said series of predefined points on said patient body comprises three points.

5. A system according to claim 1, wherein said series of predefined points on said body comprises one or two points, and wherein corrections to patient alignment is solely translational.

6. A system according to claim 1, wherein said movable reference object comprises an infrared emitting probe extending along a longitudinal axis.

7. A system according to claim 5, wherein said infrared emitting probe comprises at least one light-emitting diode disposed on said infrared emitting probe.

8. A system according to claim 6, wherein said at least one light-emitting diode includes a series of light-emitting diodes aligned on said infrared emitting probe, and said localizer is adapted to determine the orientation of said probe based on the alignment of said light-emitting diodes.

9. A system according to claim 1 further comprising a positioning system for supporting and moving said patient, wherein said positioning system comprises a control system, wherein said control system of said positioning system is connected to said localizing system for receiving position information of said treatment target, wherein said control system is loaded with the position information of said iso-center of said therapeutic radiation treatment device, and wherein said control system is further programmed to control said positioning system to position said treatment target with respect to said iso-center of said therapeutic radiation treatment device.

10. A system according to claim 9, wherein said positioning system is adapted to move said patient in six degrees of freedom.

11. A system according to claim 9, wherein said positioning system is adapted to move said patient in fewer than six, but more than two, degrees of freedom.

12. A system according to claim 9, wherein the positioning system comprises:
   a base member;
   a plate member rotatably mounted on said base member;
   a first arm having a first end rotatably attached to said plate member, and a second end;
   a second arm having a first end rotatably attached to the second end of said first arm, and a second end; and
   a supporting means for supporting a patient thereon, wherein said supporting means is rotatably attached to said second end of said second arm.

13. A treatment target positioning system according to claim 12, wherein said base member is rotatably mounted on a plinth.

14. A therapeutic radiation treatment system includes the treatment target positioning system of claim 1, wherein said therapeutic radiation treatment system further includes a therapeutic radiation treatment device for generating therapeutic radiation.

15. A therapeutic radiation treatment system according to claim 14, wherein said therapeutic radiation treatment device comprises a gantry-based LINAC system.

16. A therapeutic radiation treatment system according to claim 14, wherein said therapeutic radiation treatment device comprises a robotic-based LINAC system.

17. A therapeutic radiation treatment system according to claim 14 further comprising a simulation system, wherein said simulation system has an iso-center which is calibrated to the iso-center of the therapeutic radiation treatment device.

18. A system according to claim 1, wherein said positioning system is programmed to periodically or continuously adjust the position of said treatment target to maintain said treatment target being aligned with said iso-center of said therapeutic radiation treatment device.

19. A system according to claim 1, wherein said intersection point of said laser beams is coincident with said iso-center of said therapeutic radiation treatment device.

20. A system according to claim 1, wherein said positioning system includes an immobilization device constructed to fit a patient's body curve for holding said patient.

21. A system according to claim 20, wherein said immobilization device is made from a moldable material.

22. A treatment target positioning system for determining the position of a treatment target in a treatment area within a patient's anatomy and aligning the treatment target in the treatment area with an iso-center of a therapeutic radiation treatment device, said treatment target positioning system comprising:
   means for generating laser beams, which are directed to and intersect at the iso-center of said therapeutic radiation treatment device;
   a localizing system comprising:
      a). a movable reference object comprising a distal tip;
      b). a localizer comprising a computer system and at least one detector for detecting and determining the position of said moveable reference object in a treatment coordinate system when said moveable reference object is positioned at a series of positions, wherein the position of the distal tip of the movable reference object with respect to a geometry of said reference object is loaded in the computer system of said localizer, wherein said computer system of said localizer is adapted to determine the position of the distal tip in said treatment coordinate system based on the position of said movable reference object and the position of said distal tip with respect to the geometry of said reference object; and
   a positioning system for supporting and moving said patient, wherein said positioning system comprises a control system, which is connected to said localizing system for receiving position information of said movable reference object,
   wherein said movable reference object is adapted to be positioned at a series of predefined points on said patient body to determine the position of said series of points in said treatment coordinate system by said localizer,
   wherein said series of predefined points on said patient body are obtained in a pre-treatment process, said predefined points representative of intersection points of said laser beams with an exterior of the patient's body when said treatment target in said treatment area is positioned coincident with said iso-center of said therapeutic radiation treatment device in said pre-treatment process, and
   wherein said control system is programmed with trajectory information of said laser beams, and wherein said controller system is programmed to control said positioning system to align each of said series of points on said patient body to an associated laser beam.

23. A treatment target positioning system for determining the position of a treatment target in a treatment area within a patient's anatomy to allow alignment of the treatment target with the iso-center of a therapeutic radiation treatment device, said treatment target positioning system comprising:
   means for generating laser beams, which are directed to and intersect at an intersection point, wherein the location of said intersection point with respect to the iso-center of the therapeutic radiation treatment device is determinable;
   a localizing system comprising:
      a). a movable reference object comprising a distal tip;
      b). a localizer comprising a computer system and at least one detector for detecting and determining the position of said moveable reference object in a treatment coordinate system when said moveable reference object is positioned at a series of positions, wherein the position of the distal tip of the movable reference object with respect to a geometry of said reference object is loaded in the computer system of said localizer, wherein said computer system of said localizer is adapted to determine the position of the distal tip in said treatment coordinate system based on the position of said movable reference object and the position of said distal tip with respect to the geometry of said reference object; and a positioning system for supporting and moving said patient, wherein said positioning system comprises a control system, wherein said movable reference object is adapted to be positioned at a series of predefined points on said patient body to determine the position of said series of points in said treatment coordinate system by said localizer, wherein said series of predefined points on said patient body are obtained in a pre-treatment process, said predefined points representative of intersection points of said laser beams with the exterior of the patient's body when said treatment target in said treatment area is positioned coincident with said intersection point of said laser beams, wherein said computer system of said localizer is programmed with a software for determining the position of said treatment target in said treatment coordinate system based on the position information of said series of said predefined points on said patient body received from said localizing system wherein said control system of said positioning system is connected to said localizing system for receiving position information of said treatment target, wherein said control system is loaded with the position information of said iso-center of said therapeutic radiation treatment device, and wherein said control system is further programmed to control said positioning system to position said treatment target with respect to iso-center of said therapeutic radiation treatment device.

24. A method of determining a position of a treatment target in a treatment area within a patient's anatomy and positioning said treatment target to an iso-center of a therapeutic radiation treatment device, said method comprising:

A). determining positions of a series of markings on the patient body in a treatment coordinate system, wherein said markings on the patient body are obtained in a pre-treatment process, said markings representative of intersection points of laser beams with an exterior of the patient's body when said treatment target in said treatment area is positioned at a point, wherein the location of said point with respect to said iso-center of said therapeutic radiation system is determinable, wherein said laser beams are generated by a room beam coordinate system and are directed to said point, wherein determining comprises:

sequentially positioning a distal tip of a movable reference object at said markings; and determining the position of said movable reference object by a localizer, said localizer comprising at least one detector and a computer system for detecting and determining the position of said moveable reference object in said treatment coordinate system when said moveable reference object is positioned sequentially at said markings, B. determining the position of said treatment target in said treatment coordinate system based on the positions of said series of markings on said patient body by using a computer system, comprising loading the position of the distal tip of the movable reference object with respect to a geometry of said movable reference object into the computer system of said localizer, wherein said computer system of said localizer is adapted to determine the position of the distal tip in said treatment coordinate system based on the position of said movable reference object and the position of said distal tip with respect to the geometry of said reference object; and C. positioning said treatment target to said iso-center of said therapeutic radiation treatment device by a positioning system, said positioning system having a computer system loaded with position information of said treatment target and position information of said iso-center of said therapeutic radiation treatment device.

25. A method according to claim 24, wherein said point whose location with respect to said iso-center of said therapeutic radiation system is determinable is coincident with said iso-center of said therapeutic radiation treatment device.

26. A method according to claim 24, wherein said localizer comprises an infrared localizer.

27. A method according to claim 24, wherein said at least one detector comprises at least one infrared camera.

28. A method according to claim 24, wherein said movable reference object comprises an infrared emitting probe extending along a longitudinal axis.

29. A method according to claim 28, wherein said infrared emitting probe comprises at least one light-emitting diode disposed on said infrared emitting probe.

30. A method according to claim 29, wherein said at least one light-emitting diode includes a series of light-emitting diodes aligned on said infrared emitting probe, and said localizer is adapted to determine the orientation of said probe based on the alignment of said light-emitting diodes.

31. A method according to claim 24, wherein said laser beams comprises three laser beams, and said series of predefined points on said patient body comprises three points.

32. A method according to claim 24, wherein said series of predefined points on said patient body comprises one or two points.

33. A method according to claim 24, wherein said positioning system is adapted to move said patient in six degrees of freedom.

34. A method according to claim 24, wherein said positioning system includes a supporting means molded to fit a patient's body curve.

35. A method according to claim 24, wherein the positioning system comprises:
 a base member;
 a plate member rotatably mounted on said base member;
 a first arm having a first end rotatably attached to said plate member, and a second end;
 a second arm having a first end rotatably attached to the second end of said first arm, and a second end; and
 a supporting means for supporting a patient thereon, wherein said supporting means is rotatably attached to said second end of said second arm.

36. A method according to claim 24, wherein said positioning system is programmed to periodically adjust the position of said treatment target to maintain said treatment target being aligned with said iso-center of said therapeutic radiation treatment device.

37. A method according to claim 24, wherein said method further comprises a pre-treatment process for obtaining said markings on said patient body, said pre-treatment process comprises:

positioning said treatment target within said treatment area to an iso-center of a simulation system; and marking a series of intersection points where laser beams of a room beam coordinate system intersect with an exterior of the patient's body, wherein said laser beams are directed to said iso-center of said simulation system.

38. A method according to claim 37, wherein said positioning said treatment target within said treatment area to an iso-center of a simulation system comprises:

obtaining near real time image containing information regarding the near real time position of said treatment target with respect to said treatment coordinate system;

comparing the position of said treatment target, as shown in said near real-time image data, with the position of said iso-center of said simulation system; and generating at least one motion command signal for implementing one or more corrective motions of said positioning system, said corrective motions aligning said treatment target with said iso-center of said simulation system.

39. A method according to claim 37, wherein said iso-center of said simulation system used in said pre-treatment process is calibrated with the iso-center of the therapeutic radiation treatment device.

40. A method according to claim 37, wherein said simulation system used in said pre-treatment process and said therapeutic radiation treatment device are the same treatment device.

41. A method of determining the position of a treatment target in a treatment area within a patient's anatomy and positioning the treatment target to an iso-center of a therapeutic radiation treatment device, said method comprising a pre-treatment process and a real treatment positioning process, wherein said pre-treatment process comprises:
a). positioning a treatment target within said treatment area to a point, wherein the location of said point with respect to the iso-center of the therapeutic radiation treatment device is determinable; and
b). marking a series of intersection points where laser beams of a room beam coordinate system intersect with an exterior of the patient's body, wherein said laser beams are directed to said point; and wherein said real treatment positioning process comprises:
c). determining the position of said intersection points marked on the exterior of the patient body with respect to the room beam coordinate system comprising:
sequentially positioning a distal tip of a movable reference object at said markings; and
determining the position of said movable reference object by a localizer, said localizer comprising at least one detector and a computer system for detecting and determining the position of said moveable reference object in said treatment coordinate system when said moveable reference object is positioned sequentially at said markings;
loading the position of the distal tip of the movable reference object with respect to a geometry of said movable reference object into the computer system of said localizer, wherein said computer system of said localizer is adapted to determine the position of the distal tip in said treatment coordinate system based on the position of said movable reference object and the position of said distal tip with respect to the geometry of said reference object;

d). determining the position of the treatment target with respect to the room beam coordinate system; and
e). positioning said treatment target to said iso-center of said therapeutic radiation treatment device.

42. A method according to claim 41, wherein said simulation system used in said pre-treatment process and said therapeutic radiation treatment device used in said real treatment positioning device are the same treatment device.

43. A method according to claim 41, wherein said room beam coordinate system includes three laser beams directed to said point whose location with respect to said iso-center of said therapeutic radiation system is determinable, and said series of intersection points includes three intersection points.

44. A method according to claim 41, wherein said room beam coordinate system includes one or two laser beams directed to said point whose location with respect to said iso-center of said therapeutic radiation system is determinable, and said series of intersection points includes one or two intersection points.

45. The method of claim 24, wherein the positioning system further comprises a couch, and wherein positioning said treatment target to said isocenter of said therapeutic radiation treatment device comprises automatically positioning said treatment target using the computer system coupled with the couch on which the patient resides.

46. The method of claim 45, wherein the positioning system further comprises a robot couch assembly having the couch.

47. The method of claim 41, wherein positioning said treatment target to said isocenter of said therapeutic radiation treatment device comprises automatically positioning said treatment target using a computer system coupled with a couch on which the patient resides.

48. The method of claim 45, wherein the couch is a robot couch assembly and wherein positioning comprises control movement of the robot couch assembly in six degrees of freedom using the computer system.

49. A method of patient alignment in a radiation treatment system, comprising:

determining a first patient position, during pre-treatment simulation, in a room coordinate system comprising localizing a series of intersection points where laser beams of the room beam coordinate system intersect with an exterior of the patient's body by touching the series of intersection points with an infrared emitting probe detectable by an infrared camera;

computing the first patient position in a treatment coordinate system from the room coordinate system;

determining a second patient position in the room coordinate system at treatment delivery, wherein the series of intersecting points comprises three points to determine translation and rotation of the second patient position;

computing the second patient position in the treatment coordinate system from the room coordinate system; and automatically positioning the patient, at treatment delivery, to the first patient position based on comparing the first and second patient positions.

50. The method of claim 49 wherein determining the second patient position at treatment delivery comprises identifying the series of intersection points with the infrared emitting probe.

51. The method of claim 50, wherein, prior to determining the first patient position in the room coordinate system, the method further comprises positioning a treatment target within the patient to an iso-center of an imaging system of the radiation treatment system, wherein the laser beams are directed to the iso-center.

52. The method of claim 49, wherein the treatment delivery system comprises a robot couch assembly, and wherein automatically positioning comprises controlling movement of a robot couch assembly on which the patient resides.

53. The method of claim 52, wherein the robot couch assembly is configured to move in six degrees of freedom.

54. The method of claim 49, wherein the patient is automatically positioned to the first position at treatment delivery without the use of a fixed reference device to determine the first patient position during pre-treatment simulation in the room coordinate system.

* * * * *